US007810504B2

(12) United States Patent
Guzman

(10) Patent No.: US 7,810,504 B2
(45) Date of Patent: Oct. 12, 2010

(54) SYSTEM AND METHOD FOR WEARABLE USER INTERFACE IN COMPUTER ASSISTED SURGERY

(75) Inventor: Jose F. Guzman, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1009 days.

(21) Appl. No.: 11/319,960

(22) Filed: Dec. 28, 2005

(65) Prior Publication Data

US 2007/0200863 A1 Aug. 30, 2007

(51) Int. Cl.
*A61B 19/00* (2006.01)

(52) U.S. Cl. ........................................................ 128/897

(58) Field of Classification Search ................. 128/897, 128/899; 606/1, 169, 203; 345/156, 158; 340/407.1, 825.19; 341/20, 21, 379.55
See application file for complete search history.

(56) References Cited

U.S. PATENT DOCUMENTS

| | | | | |
|---|---|---|---|---|
| 4,221,975 | A * | 9/1980 | Ledniczki et al. | 307/116 |
| 5,191,197 | A * | 3/1993 | Metlitsky et al. | 235/462.44 |
| 5,230,623 | A | 7/1993 | Guthrie et al. | |
| 5,305,181 | A * | 4/1994 | Schultz | 361/679.03 |
| 5,416,310 | A * | 5/1995 | Little | 235/462.44 |
| 5,576,727 | A | 11/1996 | Rosenberg et al. | |
| 5,786,804 | A * | 7/1998 | Gordon | 345/158 |
| 5,995,077 | A | 11/1999 | Wilcox et al. | |
| 6,057,540 | A * | 5/2000 | Gordon et al. | 250/221 |
| 6,137,675 | A * | 10/2000 | Perkins | 361/679.03 |
| 6,424,335 | B1 * | 7/2002 | Kim et al. | 345/158 |
| 6,646,541 | B1 | 11/2003 | Wang et al. | |
| 6,781,570 | B1 | 8/2004 | Arrigo et al. | |
| 6,853,293 | B2 * | 2/2005 | Swartz et al. | 340/5.92 |
| 2003/0159141 | A1 * | 8/2003 | Zacharias | 725/37 |
| 2004/0169673 | A1 | 9/2004 | Crampe et al. | |
| 2004/0240163 | A1 * | 12/2004 | Adams et al. | 361/681 |
| 2005/0052412 | A1 | 3/2005 | McRae et al. | |
| 2005/0164684 | A1 | 7/2005 | Chen et al. | |
| 2005/0206583 | A1 | 9/2005 | Lemelson et al. | |
| 2005/0233859 | A1 | 10/2005 | Takai et al. | |
| 2006/0033710 | A1 * | 2/2006 | Bajramovic | 345/156 |
| 2006/0142739 | A1 * | 6/2006 | DiSilestro et al. | 606/1 |

FOREIGN PATENT DOCUMENTS

| | | |
|---|---|---|
| DE | 100 33 680 | 1/2002 |
| WO | WO 98/08062 | 2/1998 |
| WO | WO 2004/001569 | 12/2003 |
| WO | WO 2005/092230 | 10/2005 |
| WO | WO 2006/115347 | 11/2006 |

* cited by examiner

*Primary Examiner*—John P Lacyk
(74) *Attorney, Agent, or Firm*—Maginot, Moore & Beck

(57) ABSTRACT

A computer assisted surgery system includes a display for visual rendering of surgical data, a processor for receiving a control signal and performing operations associated with the control signal and for controlling the surgical data rendered by the display, and a wearable input device in communication with the processor. The wearable input device in one embodiment includes a mounting surface on a first side of the input device for mounting to a body portion of a user and a sensor assembly located on the side of the input device opposite the mounting surface.

11 Claims, 5 Drawing Sheets

54
56
46
18
44
38
48
32
42
40
34

SYSTEM AND METHOD FOR WEARABLE USER INTERFACE IN COMPUTER ASSISTED SURGERY

FIELD OF THE INVENTION

This invention relates to computer assisted surgery and, more particularly, to user interface devices used in computer assisted surgery.

BACKGROUND

The use of computer assisted surgery systems (CAS systems) or image guided surgery systems is becoming widespread. In a typical CAS system, a computer and a position measurement device are used in order to measure the position of surgical instruments, devices and a body portion of the patient. CAS systems also incorporate a memory means to store medical data such as e.g. X-rays, computertomographs or magnetic resonance images (MRIs). The medical images may be gathered pre-operatively or intraoperatively.

Computer assisted orthopaedic surgery systems include a) computeltomogram (CT) based systems, may be used preoperatively to establish a three-dimensional anatomical model of a bone or bone fragment that is referenced during the surgical procedure to identify the respective bone or bone fragment through a landmark based or surface based registration or matching procedure; b) CT based and fluoroscopy systems, which use the same method as CT based systems to establish a three-dimensional anatomical model, whereby the preoperative CT of a bone or bone fragment is registered or matched to the intraoperative respective bone or bone fragment through using a surface model of the bone or bone fragment and its projections in the planes of the fluoroscopic images; and c) fluoroscopy based systems, which use calibrated fluoroscopes to generate undistorted images of a bone or bone fragment and virtual geometric representations of the projection of surgical tools.

When used during a surgical procedure, most CAS systems require input from the surgeon in order to specify the data to be shown or to alter the program flow. The surgical data may include data stored preoperatively as well as data obtained during the surgery, such as blood pressure, heart rate, oxygen levels, etc. Many systems rely upon a non-sterile assistant to input instructions at a keyboard or with a mouse, but these systems are inefficient and risk miscommunication.

In other systems, an input device is physically located within the operating room. The input device is generally covered with a plastic material to provide a physical barrier against the spread of germs. When control of the CAS is required, the surgeon or other personnel within the operating room go to the location of the input device and operate the device. This approach is cumbersome since it requires a dedicated location for the input device within an already crowded operating room. Moreover, the movement of personnel to the location of the input device creates undesired activity within the operating room.

Some systems have attempted to address the shortcomings of the above described approach in various ways. One such approach is to provide an input device in the form of a foot operated device. Of course, this type of a device becomes a hazard when personnel are moving about the location of the foot operated device. Moreover, the foot operated devices do not provide for cursor control.

What is needed, therefore, is a CAS input device that allows personnel to control the CAS during an operation.

What is further needed is a CAS input device that does not require personnel to move to a specific location within the operating room to operate the device.

What is also needed is a CAS input device that is conveniently located for ease of access and which allows for the control of the cursor on a display.

What is needed is a CAS input device that does not present a hazard to individuals moving about an operating room.

SUMMARY

A method of performing a medical procedure in accordance with the invention includes mounting an input device on a user, establishing a communications link between the input device and a computer, placing a light permeable garment over the input device, sensing with the input device a desired cursor control input through the light permeable material, generating a cursor control signal based upon the control input, and controlling the visual rendering on a display based upon the cursor control signal.

In one embodiment, a computer assisted surgery system includes a display for visual rendering of surgical data, a processor for receiving a control signal and performing operations associated with the control signal and for controlling the surgical data rendered by the display, and a wearable input device in communication with the processor for receiving input from a user wearing the interface device, converting the input into the control signal and transmitting the control signal to the processor.

In a further embodiment, a computer assisted surgery system includes a display for visual rendering of surgical data, a processor for receiving a control signal and performing operations associated with the control signal and for controlling the surgical data rendered by the display, and a wearable input device in communication with the processor. The wearable input device includes a mounting surface on a first side of the input device for mounting to a body portion of a user, and a sensor assembly located on the side of the input device opposite the mounting surface.

The above-described features and advantages, as well as others, will become more readily apparent to those of ordinary skill in the art by reference to the following detailed description and accompanying drawings.

DETAILED DESCRIPTION

Figure 1:
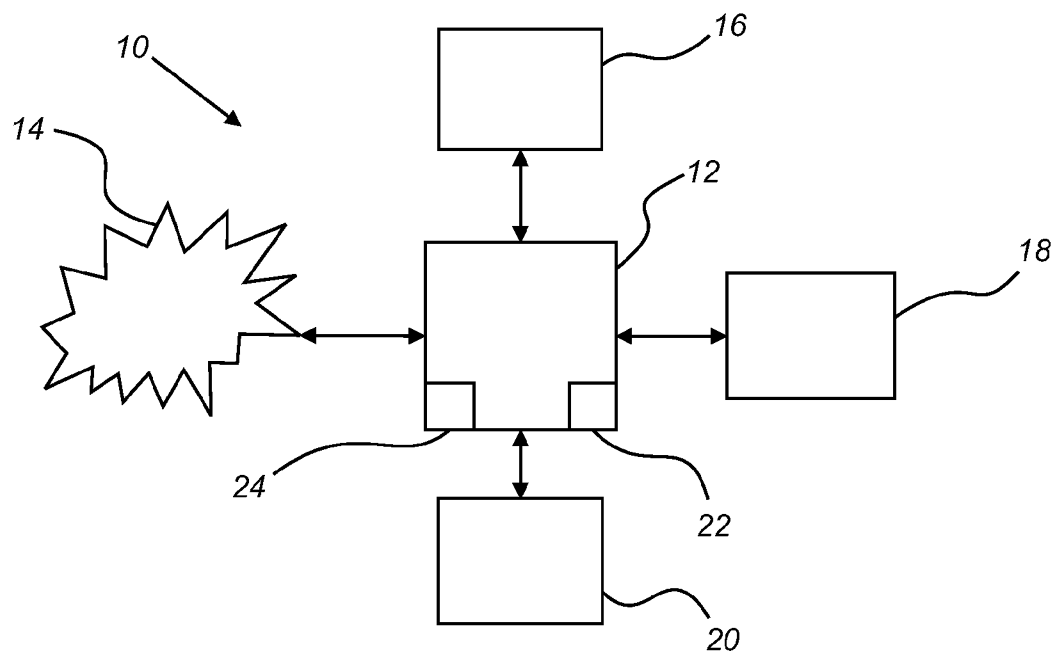
FIG. 1 depicts a block diagram of a computer assisted surgery system including a wearable input device with an optical sensor in accordance with principles of the present invention.

FIG. 1 illustrates a block diagram of a computer system 10 for use in computer assisted surgery. The computer system 10 includes a surgical computer 12 which is in communication with a network 14, a display 16 and an input device 18. The surgical computer 12 may further be in communication with other peripherals such as peripheral 20. Peripheral 20 may be an external memory, a surgical device, a printer, or other desired device.

The surgical computer 12 includes an internal processor 22 and an internal memory 24 in communication with the processor 22. The internal memory 24 includes instructions which allow the surgical computer 12 to interface with the network 14 and various peripherals such as input device 18, display 16 and peripheral 20 as is known in the art. The internal memory 24 further includes instructions which, when executed by the processor 22, allow the surgical computer 12 to be used to assist in performance of a surgical operation.

The network 14 in this embodiment is a local area network for a medical facility which provides a surgeon or other medical personnel with access to resources useful in the conduct of a particular operation. By way of example, the resources may include medical records, the internet, and video-conferencing capability. Alternatively, some or all of the resources may be provided in the internal memory 22. Communication between the network 14 and the surgical computer 12 may be accomplished using cables, optical communications, radio frequency (RF) communications or any other desired mode of transferring data.

The display 16 in this embodiment is a cathode ray tube (CRT) used for rendering graphical representations of data under control of the surgical computer 12. Any appropriate type of display may be used in accordance with the present invention including liquid crystal diode (LCD) displays, light emitting diode (LED) displays and heads-up displays (HUD).

Figure 2:
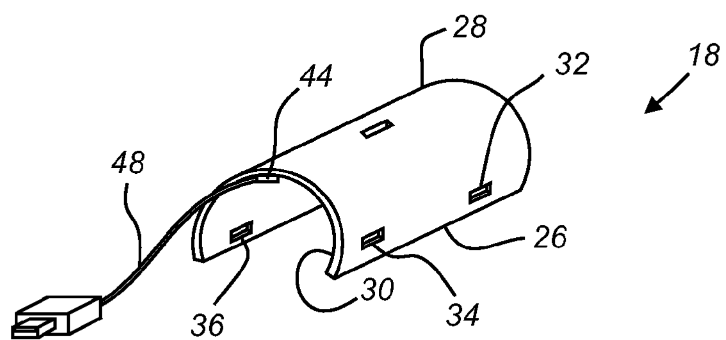
FIG. 2 depicts a perspective view of the input device of FIG. 1.

FIG. 2 depicts a perspective view of the input device 18. The input device 18 includes a body 26 with an outer side 28 and an inner side 30. A plurality of slots 32, 33 (see FIG. 5), 34 and 36 extend through the body 26 from the inner side 30 to the outer side 28. The slots 32, 33, 34 and 36 may be used with one or more straps to mount the input device 18 onto a user. By way of example, in FIG. 3 the input device 18 is mounted onto the forearm 38 of a user by a strap 40 extending between the slot 34 and the slot 36 and a strap 42 extending between the slot 32 and slot 33 (see FIG. 5).

The straps 40 and 42 may be made of a material such as VELCRO®. The use of VELCRO® straps allows a single input device 18 to be used with forearms of various sizes. Nonetheless, it may be desired to provide a plurality of input devices configured with different curvatures. More specifically, the inner side of the input devices may have different radii of curvature. In such embodiments, small, medium and large curvature input devices may be provided so as to comfortably fit a number of different sized users. Alternatively, the input device may include a body made of expandable material. In this alternative embodiment, the body of the input device stretches to conform to the size of the user's forearm so as to maintain the input device snuggly in position on the user's forearm.

The input device 18 further includes a USB connection, or connector, 44 and an optical sensor well 46 for placement of a sensor assembly. The USB connection 44 provides a path for communications with the surgical computer 12 and further provides power to the input device 18. The USB connection 44 may be connected to the surgical computer 12 by a USB cable 48. Alternatively, the USB connection 44 may be connected to an RF transmitter so as to provide a wireless connection. Of course, the input device may be a self contained wireless unit with an internal power supply. Alternatively, a separate power supply may be used so that the battery or other power source may be placed at a different location on the body of a user, such as on a belt. This minimizes the weight of the input device 18 and facilitates replacement of the power source as well as facilitating the provision of redundant power sources.

Figure 4:
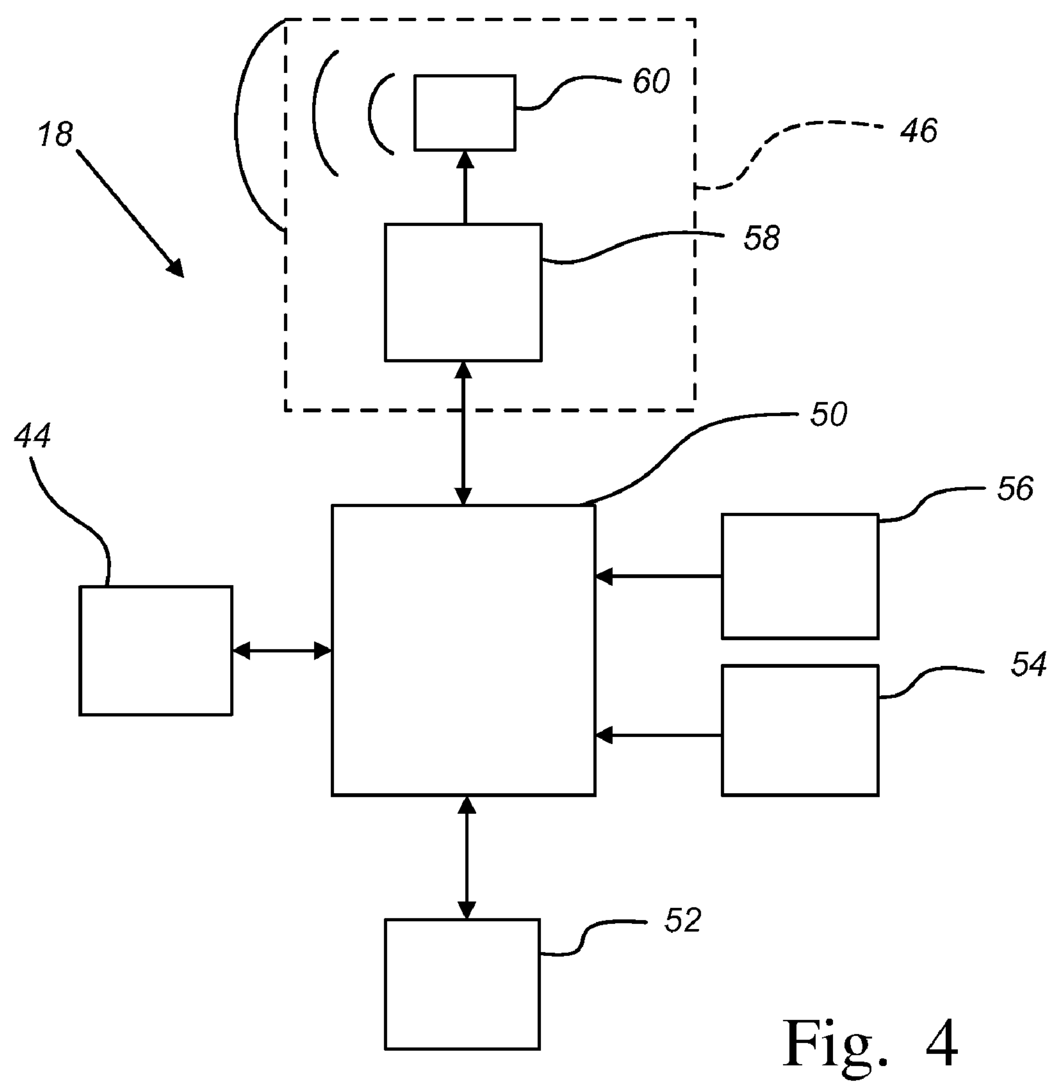
FIG. 4 depicts a block diagram of the input device of FIG. 1.

A block diagram of the input device 18 is depicted in FIG. 4. The input device 18 includes a micro controller 50, the USB connector 44, a USB connector 52, two mechanical switches 54 and 56, an optical sensor 58 which controls an LED 60. The optical sensor 58 and the LED 60 are located in the optical sensor well 46 shown in FIG. 2. In this embodiment, the optical sensor 58 includes a charged-coupled device (CCD) array and a lens for focusing reflected light onto the array. Alternatively, the optical sensor 58 can have a photosensitive element other than a CCD array, such as a number of photo-diodes or photo-transistors.

The input device 18 allows a user to interact (e.g., effect cursor movement, scrolling, or button action) with the surgical computer 12. Movement relevant to the input device 18 is detected by a sensor assembly and translated into position data, and is communicated to the surgical computer 12 via the USB connection 44. In this embodiment, light from the LED 60 reflects off of a surface moving past the optical sensor well 46, and causes an image of the surface or object to be generated. This image is detected by optical sensor 58.

The direction and distance of movement can be determined by a series of such detected images. In one embodiment, the reflected images are focused by a lens onto the CCD array. Each image can be represented by a number of pixels on the CCD array. A difference between consecutive images indicates movement, while no difference between consecutive images indicates lack of movement. The image difference data is determined by the microcontroller 50 and communicated to the surgical computer 12 which in turn controls the position of a cursor rendered on the display 16.

The optical sensor 58 is calibrated such that the movement of material used in a surgical gown or other garment is not detected. By way of example, while surgical garments are typically impermeable to fluids, they will allow, to some extent, energy in the form of light to pass through. Accordingly, an optical sensor, such as one available in a PocketMouse™ Wireless Mini or a PocketMouse Optical Mini computer mouse commercially available from Kensington Computer Products Group, of Redwood Shores, Calif., does not detect the movement of the material. When the user's hand is moved over the top of the optical sensor well 46 and surgical gown material, however, the movement of the hand is detected. Accordingly, the input device 18 may be worn and operated beneath a surgical gown. Additionally, because the use of a material that is somewhat light permeable allows a user to easily determine the location of the optical sensor well 46 even when the optical sensor well 46 is covered by the material.

Figure 3:
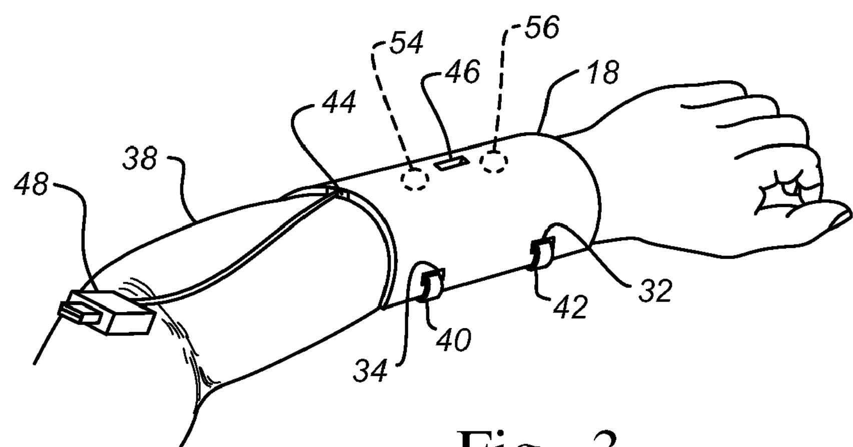
FIG. 3 depicts a perspective view of the input device of FIG. 1 mounted on the left forearm of a user in accordance with principles of the present invention.

The USB connection 44 is used when the input device 18 is mounted on the left forearm of a user as shown in FIG. 3. This allows the USB cable 48 to be directed toward the back of the user and away from the hand of the user. When the USB connection 44 is used, movement of an appendage such as a hand or finger in the direction generally defined by the direction from the elbow toward the wrist over the optical sensor well 46 is detected by the optical sensor 58 and translated by the microcontroller 50 into a signal corresponding to a desired movement of a cursor rendered on the display 16 from a first location on the display 16 to a position to the right of the first location.

Similarly, movement of a hand or finger in the direction generally defined by the direction from the slot 34 to the slot 36 over the optical sensor well 46 is detected by the optical sensor 58 and translated by the microcontroller 50 into a signal corresponding to a desired movement of a cursor rendered on the display 16 from a first location on the display 16 to a higher location on the display 16.

The USB connector 52 is similar to the USB connector 44, however, the USB connector 52 is physically located at the end of the body 26 opposite to the USB connector 44. Accordingly, when the input device 18 is mounted on the right forearm of a user, the USB connector 52 may be used to avoid having any cables extending out from the input device 18 toward the hand of the user. When the input device 18 is mounted on the right arm of a user, control of the movement of a cursor on the display 16 is effected in the same manner as described above with respect to USB connector 44.

The mechanical switches 54 and 56 function in the same manner as the "left-click" and "right-click" buttons on a standard mouse. In this embodiment, the mechanical switch 54 is physically located to the left of the optical sensor well 46 and the mechanical switch 56 is physically located to the right of the optical sensor well 46. Accordingly, the microcontroller 50 translates activation of the mechanical switch 54 into a "left-click" control signal and activation of the mechanical switch 56 into a "right-click" control signal.

In embodiments having a single USB connector, operation of the input device is the same as described above. When the single USB connector device is worn on the right forearm, however, it may be desired to modify the correlation between movement sensed by the optical sensor 58 and the position of a cursor on the display 16. Specifically, using the input device 18 as an example, when the input device 18 is located on a right forearm 62 with the USB connector 44 positioned to be adjacent the wrist of the user, a USB cable connected to the connector 44 will extend, to some extent, toward the wrist of the user. Typically, this is not desired.

Figure 5:
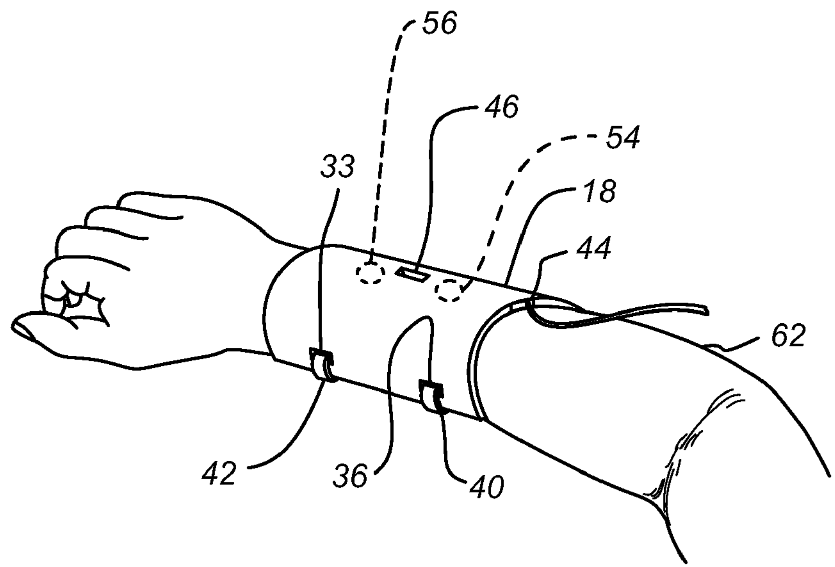
FIG. 5 depicts a perspective view of the input device of FIG. 1 mounted on the right forearm of a user in accordance with principles of the present invention.

Turning the input device 18 to position the USB connector 44 adjacent to the elbow of the user as shown in FIG. 5 causes the optical sensor well 46, when viewed by the user, to be inverted and reversed and the position of the mechanical switches 54 and 56 relative to the optical sensor 46 to be reversed. The surgical computer 12, however, may easily be programmed to account for this situation and be programmed to modify the correlation between movement sensed by the optical sensor 58 and the position of a cursor on the display 16. The alternative correlation may be activated by, for example, designating desired correlation from a configuration menu or activating a switch.

Figure 6:
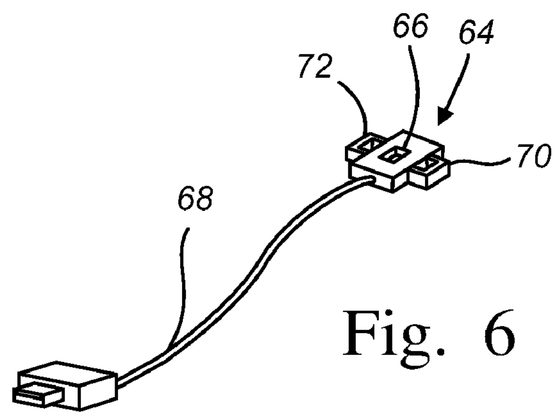
FIG. 6 depicts an alternative embodiment of a wearable input device suitable for mounting to the chest, forearm, or other appendage of a user in accordance with principles of the present invention.

In the embodiment of FIG. 2, the input device 18 is configured to conform to the general shape of the forearm of a user. In alternative embodiments, the input device 18 may be configured to be mounted on other parts of a user's body such as the chest of the user. One such embodiment is shown in FIG. 6. The input device 64 includes an optical sensor well 66, a USB output connector 68 and two loops 70 and 72. The input device 64 is relatively flat so as to be mounted comfortably on, for example, the chest of the user using the two loops 70 and 72. The input device 64 may also be mounted on the arm of the user if desired.

Figure 7:
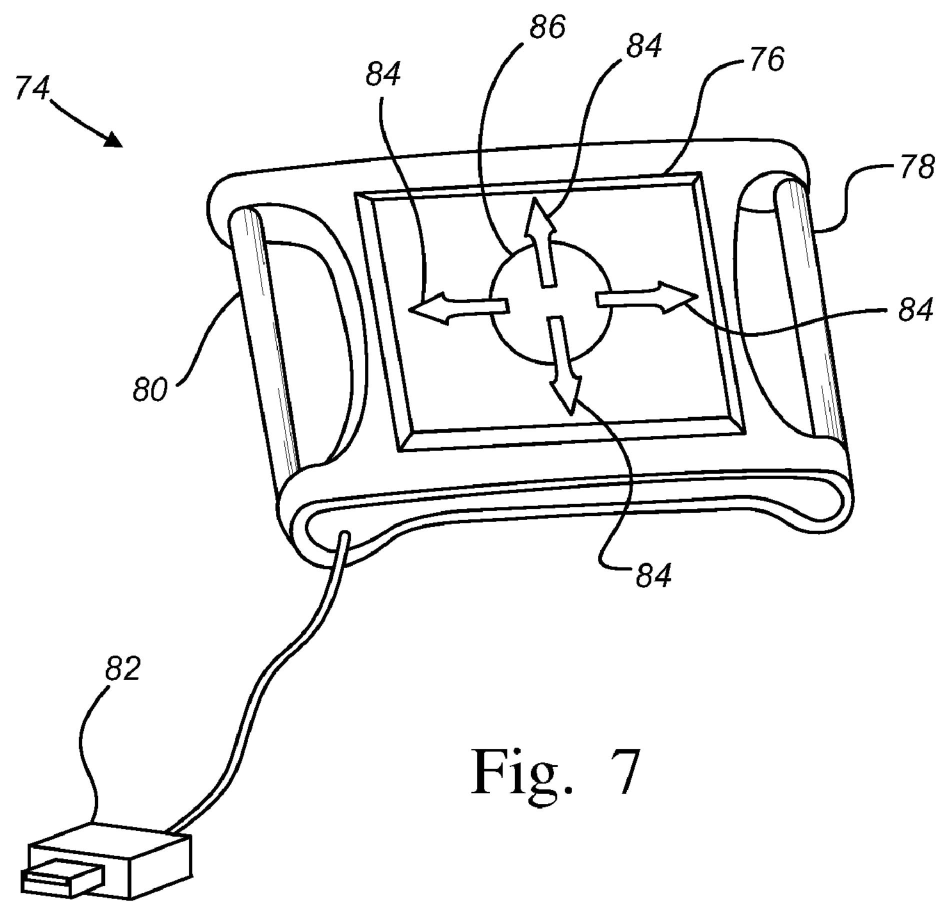
FIG. 7 depicts an alternative embodiment of a wearable input device incorporating mechanical switches suitable for mounting to the chest, forearm, or other appendage of a user in accordance with principles of the present invention.

FIG. 7 depicts an input device 74 that may be mounted on a user so as to provide input to the surgical computer 12 during a medical operation through a mechanical sensor assembly. The mechanical input device 74 includes a control pad 76, two attachment posts 78 and 80, and a USB connector 82. Desired movement of a cursor is effected by pressing the control pad 76 at a location near the head of one of the arrows 84. Pressing the control pad 76 near the outer edges of the control pad 76 in this manner causes one or more of a plurality of mechanical switches to be closed, indicating the desired direction of movement. Depressing the circle 86 causes a centrally located mechanical switch to be closed, thereby "selecting" the location on the display 16 associated with the cursor. To assist in locating the control pad 76 when it is mounted underneath a garment, the control pad 76 and/or the arrows 84 and circle 86 may be lighted.

Figure 8:
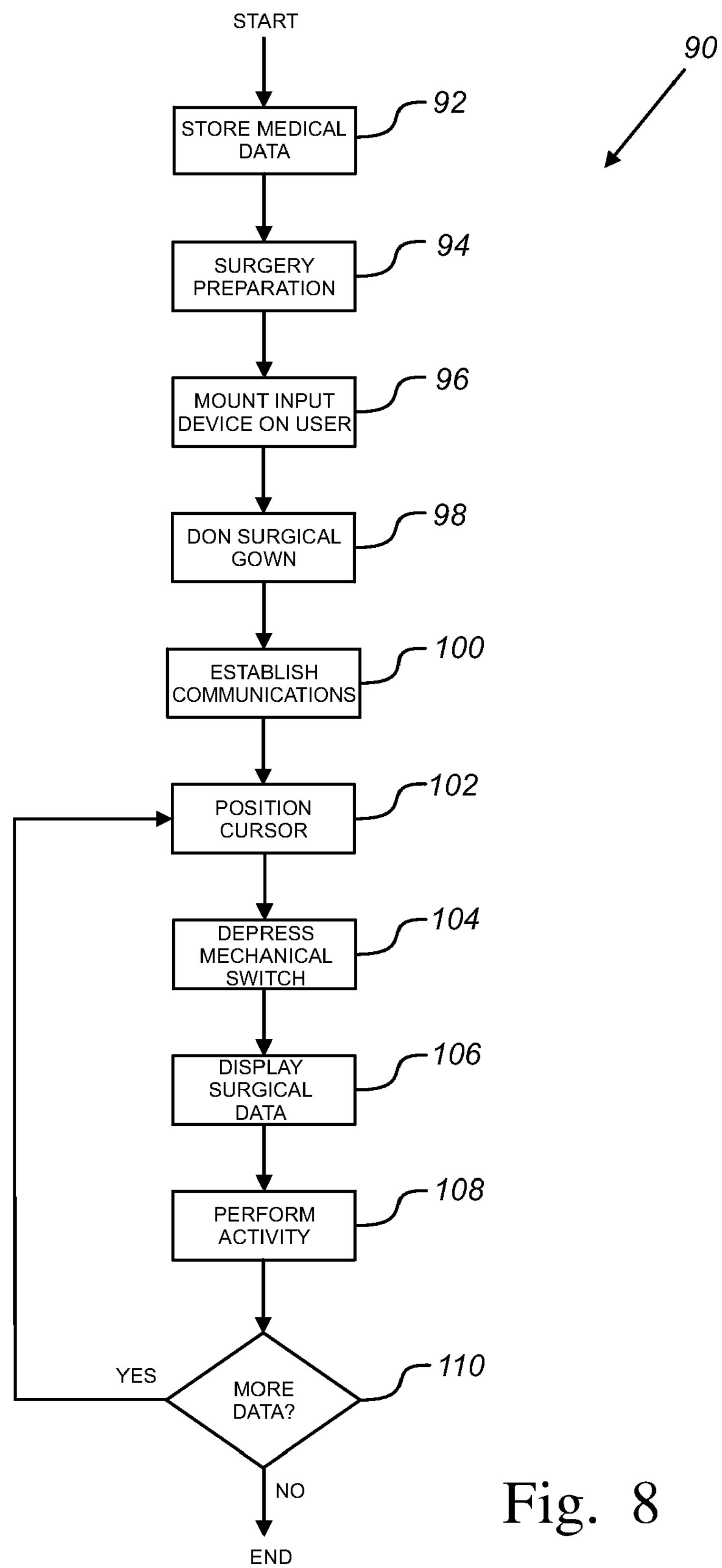
FIG. 8 shows a flow diagram of a method of performing a surgical procedure using the input device of FIG. 1 in accordance with principles of the present invention.

FIG. 8 depicts a method 90 for performing a surgical procedure using the computer assisted surgery system of FIG. 1. At the step 90, surgical data is stored in memory 24 of the host computer 12. Alternatively, the data may be stored in a memory accessible through the network 14. The data may include x-rays, steps for the planned surgical procedure, and special precautions or constraints. The materials or devices to be used in the surgical procedure, such as prosthetics, may also be identified.

The surgical team including the individual identified to operate the input device 18 who, in this example, is the surgeon, then undertake typical preparations for surgery such as sterilization, at the step 94. Next, the input device 18 is mounted on the forearm of the surgeon at the step 96. The input device 18 may be mounted on either the left forearm or the right forearm of the surgeon. In this example, the input device 18 is mounted on the right forearm of the surgeon.

In embodiments including a battery pack and or wearable transceiver, those devices are also mounted on the surgeon during this step. In this example, the input device 18 is placed upon the forearm of the user and the straps 40 and 42 are adjusted to provide a snug fit. If desired, a garment or padding may first be placed on the forearm prior to mounting the input device 18 on the forearm.

At the step 98, the surgeon dons a surgical gown which is light permeable. Communication between the input device 18 and the computer 12 is then established by connecting the USB cable 48 between the USB connector 44 and a USB connector (not shown) on the computer 12 at the step 100. The surgeon can visually verify that the input device is powered by looking for a reddish illumination on the sleeve of the surgical gown. If desired, the surgeon may modify the operational mode of the input device 18 at this point. This may be desired in single USB connector devices as discussed above.

At the step 102, the surgeon controls the position of the cursor on the display 16 by moving a hand over the illuminated area of the surgical gown. The optical sensor 58 detects the movement of the hand and generates a cursor control signal based upon the detected movement. The cursor control signal is transmitted to the computer 12 which uses the cursor control signal to control the position on the display 16 at which the cursor is rendered.

Once the cursor on the display is at the desired location, the surgeon commands the operation associated with the cursor position by depressing the mechanical switch 56 at step 104. Depression of the switch 56 is detected by the input device 18 which generates a mechanical device control signal based upon the detected depression which is transmitted to the computer 12. Based upon the location of the cursor on the display 16 and the receipt of the mechanical device control signal, the computer 12 executes a program. In this example, the executed program causes a stored surgical data file to be accessed. Thus, at the step 106, a first surgical data is displayed.

In the event the surgical data is associated with a particular activity, the surgeon performs the activity at the step 108. Such an activity may be, for example, the selection of a desired prosthetic device, selecting a desired incision location, etc. The surgeon then determines if another surgical data is needed at the step 110. If so, the method returns to step 102 so as to display a second surgical data at the step 106. If no additional surgical data is needed, the method ends.

While the present invention has been illustrated by the description of exemplary processes and system components, and while the various processes and components have been described in considerable detail, applicant does not intend to restrict or in any limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept.

I claim:

1. A computer assisted surgery system comprising:

a display for visual rendering of surgical data;

a processor for receiving a control signal and performing operations associated with the control signal and for controlling the surgical data rendered by the display; and a wearable input device in communication with the processor for receiving input from a user wearing the wearable input device, for converting the input into the control signal, and for transmitting the control signal to the processor, a memory including instructions which, when executed by the processor, causes a description of one or more steps in a surgical procedure to be rendered on the display.

2. The computer assisted surgery system of claim 1, wherein the wearable input device comprises an antenna and the control signal is transmitted to the processor using a radio frequency transmitter.

3. The computer assisted surgery system of claim 1, wherein the wearable input device comprises an optical sensor for providing an output for controlling a position of a cursor rendered on the display, the optical sensor configured to detect relative movement of a portion of the body of the user.

4. The computer assisted surgery system of claim 3, wherein;

the wearable input device comprises a first mechanical device used to generate a first mechanical device control signal and a second mechanical device used to generate a second mechanical device control signal; and the processor is programmed to perform a first control function based upon the position of the cursor when the first mechanical device control signal is received and to perform a second control function based upon the position of the cursor when the second mechanical device control signal is received.

5. The computer assisted surgery system of claim 1, wherein the wearable input device is configured to be worn upon a forearm of the user.

6. The computer assisted surgery system of claim 1, wherein the wearable input device is configured to be worn upon a chest of the user.

7. A computer assisted surgery system comprising:

a display for visual rendering of surgical data;

a processor for receiving a control signal and performing operations associated with the control signal and for controlling the surgical data rendered by the display; and a wearable input device in communication with the processor including a mounting surface on a first side of the wearable input device for mounting to a forearm of a user, and a sensor assembly located on a side of the wearable input device opposite the mounting surface a memory including instructions which, when executed by the processor, causes a description of one or more steps in a surgical procedure to be rendered on the display.

8. The computer assisted surgery system of claim 7, wherein the sensor assembly comprises a control pad including a plurality of mechanical switches.

9. The computer assisted surgery system of claim 7, wherein the sensor assembly comprises:

an energy source for projecting energy in an upwardly direction away from the mounting surface.

10. The computer assisted surgery system of claim 9, wherein the sensor assembly comprises:

a light source: and a light detecting array.

11. The computer assisted surgery system of claim 10, wherein the wearable input device further comprises:

a first mechanical switch at a first end portion of the wearable input device; and a second mechanical switch at a second end portion of the wearable input device.

* * * * *